United States Patent [19]
Radlmaier et al.

[11] Patent Number: 5,861,389
[45] Date of Patent: Jan. 19, 1999

[54] METHODS OF TREATING ANDROGEN DEFICIENCY IN MEN USING SELECTIVE AROMATASE INHIBITORS

[75] Inventors: Albert Radlmaier; Ursula-Friederike Habenicht; Friedmund Neumann, all of Berlin, Germany

[73] Assignee: Schering Aktiengesellschaft, Germany

[21] Appl. No.: 809,582

[22] PCT Filed: Sep. 22, 1995

[86] PCT No.: PCT/EP95/03733

§ 371 Date: Jun. 13, 1997

§ 102(e) Date: Jun. 13, 1997

[87] PCT Pub. No.: WO96/09057

PCT Pub. Date: Mar. 28, 1996

[30] Foreign Application Priority Data

Sep. 22, 1994 [DE] Germany .......................... 44 35 368.5

[51] Int. Cl.$^6$ .......................... A61K 31/56; A61K 31/55; A61K 31/41; A61K 31/415
[52] U.S. Cl. .......................... 514/177; 514/178; 514/214; 514/383; 514/393
[58] Field of Search .................................... 514/177, 178, 514/214, 383, 393

[56] References Cited

PUBLICATIONS

Herzog, Epilepsia, 32(Suppl. 6), pp. S34–S37, 1991.
deLignieres, Annals of Medicine, 25, pp. 235–241, Jun. 1993.
Matsumoto, Weston Journal of Medicine, 159(5), pp. 618–620, Nov. 1993
Bagatell, et al., Journal of Clinical Endocrinology and Metabolism, 78(3), pp. 711–716, Mar. 1994.
B. Lignieres, "Transdermal Dihydrotestosterone Treatment of 'Andropause'," *Ann Med*, 25(3):235–41, Jun. 1993.
A. Matsumoto, "'Andropause'—Are Reduced Androgen Levels in Aging Men Physiologically Important?," *WJM*, 159(5), Nov. 1993.
C. Bagatell et al., "Effects of Endogenous Testosterone and Estradiol on Sexual Behavior in Normal Young Men," *J. Clin. Endocrinology & Metabolism*, 78(3):711–716, Mar. 1994.
A. Herzog, "Reproductive Endocrine Considerations and Hormonal Therapy for Men with Epilepsy," *Epilepsia*, 32(Suppl. 6):S34–S37, 1991.

*Primary Examiner*—Kimberly Jordan
*Attorney, Agent, or Firm*—Millen, White, Zelane, & Branigan, P.C.

[57] ABSTRACT

Male menopause is characterized by significant decreases in serum levels of bioavailable androgens. The administration of aromatase inhibitors to men experiencing male menopause can remedy the relative androgen deficiency in men while at the same time approximating the physiological hormonal ratio of androgens to estrogens.

2 Claims, No Drawings

METHODS OF TREATING ANDROGEN DEFICIENCY IN MEN USING SELECTIVE AROMATASE INHIBITORS

This application is a 371 of PCT/EP95/03733, filed Sep. 22, 1995.

The invention relates to the new use of aromatase inhibitors for the production of a pharmaceutical agent for treating a relative androgen deficiency in men.

In men, increasing age leads to a reduction of testicular androgen production and androgen concentration in the organism. In contrast to the situation in women, in whom estrogen production drops to castration values within a comparatively short period, this takes decades in men and involves an only gradual drop. It can nevertheless be clearly demonstrated that the total concentration of testosterone in the serum in the higher age group is significantly reduced compared to the values in young men. Because of the increase in steroid hormone-binding globulin (SHBG) that coincides with the ageing process, moreover, the proportion of free, unbound, and thus biologically active testosterone drops. In addition, it is clear that the serum levels of estrogens, although they are produced from androgens by direct conversion, do not drop in the same way as a function of age. As a result, the hormonal environment is significantly altered.

In men, the hormonal environment of the sexual steroids is characterized by a significant preponderance of androgens over estrogens. While the circulating main component of androgens, testosterone, is detected in the serum in units in the range of nmol/l, the estrogen antagonist, estradiol, can be measured only in the range of pmol/l. This considerable preponderance of androgen can be detected basically in the entire late puberty period of life, but there is a clearly different intensity of this androgen dominance as a function of age. With increasing age and particularly so in those over the age of 60, there is a less pronounced emphasis of the androgen preponderance. Table 1 shows published test series in which the ratio of testosterone serum to estradiol serum was determined in a comparison of young to old men ($\geq 60$ years).

TABLE 1

Comparison of the $T/E_2$ Ratio in Serum in Young and Old Men

| Reference | Young (<60 years) | Old (>60 years) | % Δ (reduction) |
|---|---|---|---|
| Deslypere et al.[1] | 206:1 | 128:1 | −38% |
| Pirke & Dörr[2] | 324:1 | 174:1 | −46% |
| Baker et al.[3] | 372:1 | 225:1 | −31% |
| Murano et al.[4] | | | |
| a.m. | 155:1 | 98:1 | −37% |
| p.m. | 160:1 | 84:1 | −48% |

[1]Deslypere, J. P. et al., Journal of Clinical Endocrinology and Metabolism, 64, No. 1, 1987
[2]Pirke, K. M. & Doerr, P., Acta Endocrinologica, 74 (1973), 792–800
[3]Baker, H. W. G. et al., Clinical Endocrinology, 5 (1976), 349–372
[4]Murano, E. P. et al., Acta Endocrinologica, 99 (1982), 619–623

Although in the above-mentioned works, the ratio of testosterone to estradiol is indicated to some extent in considerably different orders of magnitudes—which can be attributed to the different measuring methods that are used—in older men there is clear agreement between the relative decreases in the preponderance of testosterone by 30–50% and the previous values found in young men.

The relative testosterone deficiency that occurs can have a disadvantageous effect in many respects. It is assumed that, e.g., an imbalance between androgens and estrogens that accompanies the drop in testosterone, generally at, for example, constant estrogen concentrations, is of decisive importance for the occurrence of benign prostatic hyperplasia (BPH). Regardless of the effects of estrogens, however, the relative testosterone deficiency per se can also be regarded as responsible for a number of age-related disorders. Reduction of muscle mass, accompanied by limitation of body performance capacity, reduction of bone density and in individual cases even osteoporosis, reduction of libido and potency, and psycho-vegetative disorders can be mentioned here. All above-mentioned disorders are often generically referred to as "Klimakterium virile [Male Menopause]."

The standard treatment for this syndrome, which is presumably caused by androgen deficiency, has been to supply androgens exogenically. Orally active androgens and long-chain testosterone esters with a depot effect that are to be administered intramuscularly are used. These forms of therapy are able to improve the symptoms caused by androgen deficiency, but produce an only inadequate approximation of the physiological state.

As a substance to be administered orally, either a testosterone derivative, i.e., not a natural testosterone, is given (e.g., Proviron®), or the administration is accompanied by a disproportionately large increase in dihydrotestosterone (DHT) that deviates from the physiological situation (e.g., Andriol®). Unlike testosterone, DHT seems to be the androgen component that is of great importance for the development of BPH and also of androgenetic alopecia.

In the case of depot formulations, the uneven release from the depot represents a problem that has not yet been satisfactorily resolved; it initially results in an increase of testosterone that extends significantly beyond the normal range, but toward the end of the dosage interval it leads to significantly reduced testosterone values.

It has long been known that, in addition to androgens, estrogens are also involved in the endocrine control circuit that keeps the androgen level in men constant. By administering pharmacological doses of estrogen-active substances, such as, e.g., diethylstilbestrol, it is possible in patients with prostate cancer to largely suppress the hypophyseal LH release and to reduce the testosterone level in the serum to the castration level.

From experience with use of pure antiandrogens in prostate-cancer patients who belong to the same age group as patients with male menopause, the extent of the counter-regulatory potential can be assessed. If the central inhibiting action of androgens is suppressed by pure antiandrogens such as flutamide or casodex, in this age group this results in a counterregulatory increase in the serum testosterone concentration by about 50–60% compared to the starting value. In the case of treatment that lasts for months, however, there were indications of a lessening of the activity of counterregulation in the case of the prostate-cancer patients who were treated with pure antiandrogens, i.e., the initially significantly increased androgen levels drop again (Lund and Rasmussen, 1988; Mahler and Denis, 1990: Delaere and Van Thillo, 1991).

It is noteworthy that the reduction in androgens with age is not prevented by activation of the counterregulation mechanism. The reason for this is considered to be that, on the one hand, the testicular function generally diminishes with age, but, on the other hand, the feedback mechanism is also more sensitive to sexual steroids (Deslypere, J. P. et al., Journal of Clinical Endocrinology and Metabolism, 64, No.

1, 1987). Consequently, it has to be assumed that a less pronounced counterregulation is present in older men compared to younger men (see below), and thus for long-term use a serum androgen concentration that is higher than the starting value can be expected.

In contrast, it is known that in younger men, in long-term treatment testosterone values are also effectively increased by daily treatment with antiestrogens (with considerable partial estrogenic action in each case) (Treatment of Male Infertility, Springer-Verlag Berlin, Heidelberg, New York 1982; Fuse, H. et al., Archives of Andrology 31 (1993) 139–145).

Based on theoretical considerations, antiestrogens do not seem well suited for treatment of a relative androgen deficiency in men. Thus, treatment with antiestrogens has no effect on the estrogen level since the antiestrogens block the action of estrogens on their receptor. When antiestrogens are used as receptor blockers, inadequate compliance immediately led to an adverse effect since the higher estrogen concentration can act directly on the now free receptors because of the counterregulation that takes hold.

Another drawback of antiestrogen treatment is the uncertainty as to whether the blocking of estrogen receptors in all estrogen-dependent tissues and organs is equally intense and what significance inherent estrogeneity, such as that of, e.g., the best known antiestrogen Tamoxifen, has for use in men.

This invention has the object of providing suitable substances which remedy a relative androgen deficiency in men while at the same time approximating the physiological hormonal ratio of androgens to estrogens and which avoid the above-mentioned drawbacks.

This object is achieved according to this invention by the use of at least one aromatase inhibitor for the production of a pharmaceutical agent for treating a relative androgen deficiency in men.

It has been noted that the use of aromatase inhibitors in treating a relative androgen deficiency in older men results, surprisingly enough, in a long-term increase in the androgen level.

By gradually lowering the estrogen concentration, a counterregulatory stimulation of androgen synthesis is induced. The aromatase inhibitors result in an endogenic rebalancing of the testosterone/estrogen ratio in men; as a result, the relative androgen deficiency is again compensated for.

For the purposes of this invention, aromatase inhibitors are all those compounds that prevent estrogens from being formed from their metabolic precursors by inhibiting the enzyme aromatase (inhibition of biosynthesis). As aromatase inhibitors, therefore, all compounds are suitable that are suitable as substrates for aromatase, such as, for example, the testolactone (17a-oxa-D-homoandrost-1,4-diene-3,17-dione) that is described in the "Journal of Clinical Endocrinology and Metabolism," 49, 672 (1979), the compounds androsta-4,6-diene-3,17-dione, androsta-4,6-dien-17β-ol-3-one acetate, androsta-1,4,6-triene-3,17-dione, 4-androstene-19-chloro-3,17-dione, 4-androstene-3,6,17-trione that are described in "Endocrinology" 1973, Vol. 92, No. 3, page 874, the 19-alkynylated steroids that are described in German Laid-Open Specification 31 24 780, the 10-(1,2,-propadienyl)-steroids that are described in German Laid-Open Specification 31 24 719, the 19-thio-androstane derivatives that are described in European patent application, publication no. 100 566, the 4-androsten-4-ol-3,17-dione and its esters that are described in "Endocrinology" 1977, Vol. 100, No. 6, page 1684 and U.S. Pat. No. 4,235,893, the 1-methyl-15α-alkyl-androsta-1,4-diene-3,17-dione that is described in German Laid-Open Specification 35 39 244, the 10β-alkinyl-4,9(11)-estradiene derivatives that are described in German Laid-Open Specification 36 44 358 and the 1,2β-methylene-6-methylene-4-androstene-3,17-dione that is described in European Patent Application 0 250 262.

According to this invention, selective aromatase inhibitors are preferably used for the production of a pharmaceutical agent for treating a relative androgen deficiency in men. Selective aromatase inhibitors are defined as those compounds that act as substrates for the aromatase and at the dosage used affect no enzyme other than aromatase in a clinically relevant way.

Regarded as typical selective aromatase inhibitors according to this invention are, for example, the steroidal compounds 1-Methyl-androsta-1,4-diene-3,17-dione (DE-A 33 22 285; atamestane), 4-hydroxy-4-androstene-3,17-dione (formestane) as well as the non-steroidal aromatase inhibitors (RS)-5-(4-cyanophenyl)-5,6,7,8-tetrahydro-imidazo-(1,5α)-pyridine, hydrochloride (Cancer Res., 48, pp. 834–838, 1988; fadrozole), 4-[cyano-α-(1,2,4-triazol-1-yl)-benzyl]-benzonitrile (CGS 20267), 5-[cyclopentylidene-(1-imidazolyl)-methyl]-thiophene-2-carbonitrile (EP-A 0 411 735; pentrozole), 2,2'-[5-(1H',2',4-triazol-1-yl-methyl)-1,3-phenylene]-bis(2'-methylpropionitrile) (arimidex) and (6-[1-(4-chlorophenyl)-1,2,4-triazol-1-yl)-methyl]-1-methyl-1H-benzotriazole, dihydrochloride (vorozole).

The list of selective aromatase inhibitors above is not exhaustive; other compounds that are described in the above-mentioned materials and publications, as well as all other compounds that meet the set requirements, are also considered.

Contrary to the assumption that the counterregulatory action could diminish in cases where older men are treated with an aromatase inhibitor over several months, data from longer-term studies, e.g., with atamestane on patients with BPH, show that even after treatment lasting 24 to 48 weeks, there is still a significant increase in testosterone concentration.

Table 2 shows the corresponding results of a 24-week, four-way study in comparison to placebos (100 mg/d, 300 mg/d and 600 mg/d).

TABLE 2

| | Testosterone Serum Concentration (ng/ml) with atamestane | | |
|---|---|---|---|
| Daily Dose | Previous Value | After 24 Weeks | Δ % (median ± SD) |
| Placebo | 4.13 | 4.18 | 6.00 ± 27.64 |
| 100 mg | 4.41 | 5.57 | 29.57 ± 34.70 |
| 300 mg | 4.50 | 6.15 | 40.88 ± 156.12 |
| 600 mg | 3.78 | 5.40 | 41.19 ± 37.62 |

Tables 3 and 4 show the results after a 48-week treatment.

TABLE 3

Testosterone Serum Concentration (ng/ml) with Atamestane

| Daily Dose | Previous Value | After 48 Weeks | Δ % (X ± SD) |
|---|---|---|---|
| Placebo | 4.6 | 4.1 | −0.1 ± 43.1 |
| 400 mg | 4.2 | 5.4 | 42.9 ± 53.5 |

TABLE 4

Testosterone Serum Concentration (ng/ml) with Atamestane

| Daily Dose | Previous Value | After 48 Weeks | Δ % (X ± SD) |
|---|---|---|---|
| Placebo | 4.6 | 4.6 | 2.8 ± 26.9 |
| 100 mg | 5.1 | 5.9 | 19.0 ± 36.8 |
| 300 mg | 4.7 | 6.6 | 41.7 ± 46.4 |

Gradual lowering of the estrogen concentration induces a counterregulatory stimulation of androgen synthesis. To a certain extent, there is an endogenous testosterone substitution, by which the androgen/estrogen balance is again brought back to the "youthful" range. This substantiates the results of the longer-term treatment of older men (average age above 60 years) with the selective aromatase inhibitor atamestane.

In several clinical studies, atamestane was administered at varying dosages and over periods of up to 48 weeks to men in this age group to treat an existing BPH. The results show that with atamestane treatment for patient populations, there was a significant alteration of the testosterone/estradiol ratio in favor of testosterone. Table 5 provides the testosterone/estrogen ratio before and after the administration of atamestane for patient populations from 4 studies and 7 treatment groups.

TABLE 5

Changes in the $T/E_2$ Ratio with Atamestane

| Treatment Group | Previous Value | Treatment (Time) | % Δ |
|---|---|---|---|
| 100 mg | 248:1 | 418:1 (48 weeks) | +41% |
| 300 mg | 236:1 | 440:1 (48 weeks) | +46% |
| 400 mg | 207:1 | 454:1 (48 weeks) | +54% |
| 200 mg t.i.d. | 116:1 | 214:1 (8 weeks) | +46% |
| 100 mg | 196:1 | 376:1 (24 weeks) | +48% |
| 300 mg | 199:1 | 473:1 (24 weeks) | +58% |
| 600 mg | 170:1 | 439:1 (24 weeks) | +61% |

The administration of atamestane consistently results in a resetting of the testosterone/estradiol balance in favor of the androgenic component. This action was detectable over the entire observation period up to a maximum of 48 weeks of treatment. Although the peripheral estrogen reduction at daily doses of 100 mg–600 mg was equally intense, there was a trend toward greater emphasis of the androgenic proportion at high dosages.

Assuming that the testosterone dominance that was reduced by 30–50% in the age group of patients over 60 years compared to the younger years (relative androgen deficiency) caused the symptoms of "male menopause," the goal is thus to restore the original "balance of power" between androgens and estrogens by administering a preferably selective aromatase inhibitor by stimulating endogenic testosterone substitution without the necessity of supplying hormones exogenically. Based on the understanding that the ratio prevailing in age is the result of a 30–50% reduction compared to the youthful values, i.e., is always 50–70% of the previous value, the corresponding "youthful" previous value can be calculated for each individual patient. A 70-year-old patient with a testosterone/estradiol ratio of 230:1 must accordingly be adjusted to a new balance in the range between 229:1 to 460:1, so that a preceding 30 or 50% reduction is compensated for. Table 6 shows the result of such a calculation for the patient populations of the atamestane studies that are cited in Table 4.

TABLE 6

Comparison between Calculated "Youthful" $T/E_2$ Range and Measured Values at Various Daily Atamestane Doses

| Daily Dose | Previous Value | Calculated Target Range to Compensate for a 30–50% Reduction | Value Achieved with Atamestane |
|---|---|---|---|
| 100 mg | 248:1 | 354:1 → 496:1 | 418:1 |
| 300 mg | 236:1 | 337:1 → 472:1 | 440:1 |
| 400 mg | 207:1 | 296:1 → 414:1 | 454:1 |
| 100 mg | 196:1 | 280:1 → 392:1 | 376:1 |
| 300 mg | 199:1 | 284:1 → 398:1 | 473:1 |
| 600 mg | 170:1 | 243:1 → 340:1 | 439:1 |

At a daily dose of 100 mg, the target range is generally readily met. At higher dosages, however, the result is somewhat above the target range.

Measuring the serum concentration of testosterone and estradiol can thus give early indication of whether the desired hormone balance was achieved and optionally whether dose adjustment can be undertaken.

In general, 25 to 1000 mg, preferably 50 to 600 mg, of atamestane or a biologically equieffective amount of another aromatase inhibitor is used daily to treat a relative androgen deficiency in men.

The aromatase inhibitors can be administered, e.g., orally or parenterally.

For the preferred oral administration, suitable means are especially tablets, coated tablets, capsules, pills, suspensions, or solutions that can be produced in a way that is commonly used and familiar to one skilled in the art, with the additives and vehicles that are commonly used in galenicals for the formulation of aromatase inhibitors that are to be administered orally.

The pharmaceutical agent that is produced according to the invention contains as an active ingredient per dosage unit the aromatase inhibitor atamestane at a dosage of 50 to 500 mg in addition to the commonly used additives, vehicles and/or diluents or other aromatase inhibitors at biologically equieffective dosages.

A typical composition for a formulation of the aromatase inhibitor atamestane as a tablet is presented in the example below.

EXAMPLE

| | |
|---|---|
| 100.0 mg | of 1-Methyl-androsta-1,4-diene-3,17-dione |
| 140.0 mg | of lactose |
| 70.0 mg | of corn starch |
| 2.5 mg | of poly-N-vinylpyrrolidone 25 |
| 2.0 mg | of aerosil |
| 0.5 mg | of magnesium stearate |
| 315.0 mg | Total weight of the tablet, which is produced in the usual way on a tablet press. |

When aromatase inhibitors are used for treating male menopause, the estrogen concentration is effectively lowered. The easy controllability of the treatment distinguishes treatment with an aromatase inhibitor for stimulation of endogenic testosterone production from intervention with antiestrogens. As already explained, prospective control of the treatment by early measurement of pharmacodynamic parameters is not possible with antiestrogens.

We claim:

1. A method of treating androgen deficiency in men comprising administering a selective aromatase inhibitor.

2. A method according to claim 1, wherein the selective aromatase inhibitor is atamestane, formestane, pentrozole, arimidex, fadrozole, CGS 20267 or vorozole.

* * * * *